United States Patent [19]

Johnsen

[11] 4,335,119
[45] Jun. 15, 1982

[54] QUICK-ACTING DIURETIC COMPOSITIONS

[75] Inventor: Andreas Johnsen, Griesheim, Fed. Rep. of Germany

[73] Assignee: Rohm, Pharma GmbH, Darmstadt, Fed. Rep. of Germany

[21] Appl. No.: 25,586

[22] Filed: Mar. 30, 1979

[30] Foreign Application Priority Data

Apr. 10, 1978 [DE] Fed. Rep. of Germany ....... 2815442

[51] Int. Cl.³ .................. A61K 31/505; A61K 31/52; A61K 31/625
[52] U.S. Cl. .................................... 424/229; 424/251; 424/253; 424/303; 424/321
[58] Field of Search ............... 424/229, 251, 253, 303, 424/321

[56] References Cited

U.S. PATENT DOCUMENTS 4,252,809 2/1981 Knauf .................................. 424/253

FOREIGN PATENT DOCUMENTS 2614738 10/1977 Fed. Rep. of Germany .
2700073 7/1978 Fed. Rep. of Germany .

OTHER PUBLICATIONS

Martindale, The Extra Pharm., The Pharm. Press, London, 26th Ed. 1972, pp. 633, 652–658, 668–671.
Kalliomaki, Current Therapeutic Res., vol. 11, No. 6, Jun. 1969, pp. 344–350.
Albiez, Naunyn–Schmiedeberg's, Arch. of Pharm., Supplement 1 to vol. 297, 1977, Deutsche Pharm. Gesell. Abstracts R36, Ab. No. 142.
Hropot, supra, R37, Ab. No. 148
Fellinger, Therapie mit Triamtere, Georg Thieme Verlag, Stuttgart, 1967, p. 48.
Leilich, Arzneim,–Forsch./Drug Res., vol. 30, 1980, pp. 949–953.
Testa, Drug Metab., Marcel Dekker Inc., N.Y., pp. 265–267.
Joubert, Canad. Med. Ass. J., vol. 99, Jul. 13, 1968, pp. 57–63.
Kirk–Othmer, Enc. of Chem. Tech., John Wiley, N.Y., 3rd Ed., vol. 8, p. 17.

Primary Examiner—Anna P. Fagelson
Attorney, Agent, or Firm—Oblon, Fisher, Spivak, McClelland & Maier

[57] ABSTRACT

A diuretically active pharmacological composition which comprises 4-chloro-N-furfuryl-5-sulfamoylanthranilic acid (furosemide) together with at least one compound of formula (I)

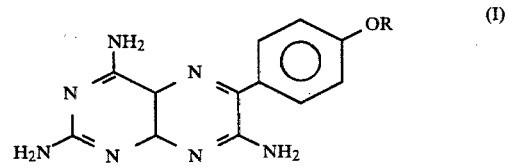

wherein R is a hydrophilic radical, capable of increasing the water solubility of the resulting compound together with a suitable pharmacological carrier.

3 Claims, No Drawings

QUICK-ACTING DIURETIC COMPOSITIONS

BACKGROUND OF THE INVENTION

1. Field of the Invention

The present invention relates to diuretically active pharmaceutical compositions useful as quick-acting diuretics.

2. Description of the Prior Art

It has been known in medical practice to use furosemide (4-chloro-N-furfuryl-5-sulfamoylanthranilic acid) for the rapid water removal in edemic conditions.

Furosemide is used above all in fluid accumulations resulting from heart insufficiency, liver cirrhosis and nephrotic syndrome. It is also useful via intravenous application in the therapy for lung and brain edemas.

Furosemide is given intravenously when a very rapid dehydration is desired or when oral application is impossible. Potassium excretion increases in furosemide treatment. When using furosemide, it is often necessary to replace potassium losses through increased oral delivery. Under the aspect of potassium loss, it is reasonable to use, in combination with furosemide, potassium retaining aldosterone antagonists or triamterenes, (2,4,7-triamino-6-phenylpteridines) (O. Schück and J. Střibrná, Handbook of Diuretic-Therapy, pp. 87–92, Urban and Schwarzenberg, Munich, Berlin, Vienna, 1971).

Researches relating to the combinations of furosemide with mercuric thiazide, hydrothiazide, and disulfonamide diuretics yielded an additive effect concerning the diuretic and salt uretic effects.

Combinations with etacrynic acid (2,3-dichloro-4-(2-methylene butyryl)-phenoxy)-acetic acid) increase the effect when both diuretics are dispensed in submaximally acting doses.

In the therapeutic practice there is therefore a need for active agents useful in the quick initiation of a forced diuresis.

Until now, furosemide has preponderantly been used for this purpose as a "high ceiling diuretic". Thiazide-diuretics, which belong to the group of the so-called "low ceiling diuretics," are not appropriate as mono-therapeutic or also in combinations, for the introduction of a forced diuresis.

The combination of furosemide with triamterenes has the advantage that the potassium loss (resulting as a consequence of the use of furosemide) is inhibited. This combination however is not appropriate for its use in intravenous delivery.

SUMMARY OF THE INVENTION

It is therefore an object of the invention to provide a quick-acting diuretic.

Another object of the invention is to provide a diuretically active pharmaceutical composition which shows small potassium-loss side-effects.*

*Quite unexpectedly the combination shows significantly reduced secretion of magnesium and calcium compared with furosemide by itself.

A further object of the invention is to provide a diuretically active pharmaceutical composition which can be delivered intravenously.

These and other objects of the invention as will hereinafter become more readily apparent have been attained by providing diuretically active pharmacological compositions which comprise furosemide (4-chloro-N-furfuryl-5-sulfamoylanthranilic acid) together with at least one compound of the formula I:

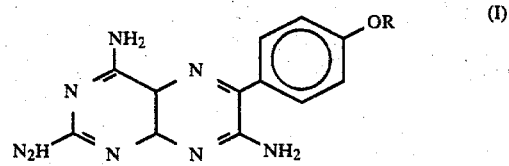

wherein R is a hydrophylic radical capable of increasing the water solubility of the resulting compound, in combination with a pharmaceutically acceptable carrier.

DESCRIPTION OF THE PREFERRED EMBODIMENTS

It has now been found that a pharmaceutical preparation, which comprises furosemide(4-chloro-N-furfuryl-5-sulfamoylanthranilic acid) and one or more pteridine compounds of the formula I as active ingredients, has exceptional properties for the quick initiation and performance of a diuresis, especially through intravenous dispensation. Especially preferred is the combination of furosemide with the sulfate half ester of 2,4,7-triamino-6-p-hydroxy-phenylpteridine and its physiologically permissible salts (hereinafter referred to as compounds of the formula IA), such as for example the non-poisonous metal salts, such as alkali- and alkaline earth salts, preferably the sodium-, and potassium salts; furthermore, the ammonium salts, especially substituted ammonium salts such as the salts of lower trialkyl amines, preferably triethylamine and trimethylamine; salts of lower alkyl pteridines, such as N-ethylpteridine, salts of procaine, of alkanolamines, such as diethylaminoethanol, dimethylaminoethanol, choline, and the like.

Under lower alkyl radicals, it is preferred to use primarily those which do not noticeably modify the water solubility, preferably those alkyl radicals which contain 1 to 4 carbon atoms, most preferably up to two carbon atoms.

The compounds of formula IA are those compounds of formula I wherein R is a $SO_3M$ radical where M stands for hydrogen or, a pharmacologically acceptable cation. Alternatively, radical R may also be a radical R' of the following formula: (the compounds where R=R' will be referred hereinafter as having general formula IB).

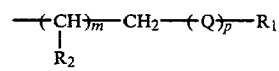

wherein $R_1$ is hydrogen, methyl- or ethyl-; $R_2$ is a OH— group, hydrogen or is an alkyl group with 1 to 4 carbon atoms; Q is oxygen, sulfur or a $NR_3$ radical, wherein $R_3$ has the same meaning as $R_1$, or Q together with the radical $R_1$, form an ammonium ion of the formula

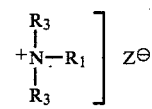

or Q together with $R_1$ form a heterocyclic radical, especially a pyrrolidinyl, piperidinyl, morpholinyl or piperazinyl, wherein $Z^-$ stands for a pharmacologically acceptable anion, and m is 0, 1, 2, or 3, p is 0 or 1; or R' is a radical $-(CH_2)_nC(O)Y$, wherein n=0, 1, 2, 3 or 4, and Y is a OH group or a pharmacologically acceptable salt thereof or Y is a $NR_4R_5$ group, wherein $R_4$ and $R_5$ independently of each other are hydrogen or an alkyl radical if necessary branched, with 1 to 4 carbon atoms or they are a radical of the formula $-(O)_r-R_6$, wherein $R_6$ is an alkyl radical of 1 to 6 carbon atoms, or they are a radical of the formula $-(CH_2)_q-R_7$, wherein q is 0, 1 or 2 and $R_7$ is a heterocyclic radical, preferably a morpholinyl, pyrrolidinyl, piperidinyl, or piperazinyl radical which may be bound through a carbon atom or a nitrogen atom; wherein in the latter case, q is not equal to 0 at the same time, and which formally form an ammonium compound through juxtaposition of a compound of the formula $R_1'Z'$, wherein $R_1'$ and $Z'$ have the same meaning as $R_1$ and Z; and r is 0 or 1, or R' stands for a radical of the formula

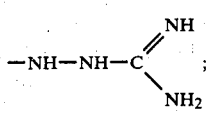

or

R' is a radical of the formula

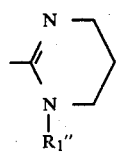

wherein $R_1''$, has the same meaning as $R_1$, or,

R' stands for a radical of the formula

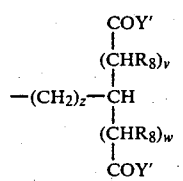

wherein

Y' has the same meaning as Y, $R_8$ is a hydrogen or an OH—group; v, w and z are 0, 1 or 2, or R' is a radical of the formula $-C(O)-(CHR_8')_s-C(O)-Y''$ wherein s=0, 1, 2 or 3, and $R_8'$ and Y'' have the same meanings as $R_8$ and Y respectively, or R' stands for a radical of the formula

wherein M is hydrogen or a physiologically acceptable cation.

Among all of these embodiments, it is preferred to use the sulfate half ester of 2,4,7-triamino-6-p-hydroxyphenyl pteridines and/or its pharmacologically acceptable salts. (Compounds IA)

These compounds are partly known from DT-OS No. 26 14 738. The compounds of the general formula I B are the subject matter of German Patent Application No. P 27 00 073. The combination of furosemide with the pteridine compounds of the general formula I B, are of particular interest.

The compositions of the present invention are superior in activity to known pharmaceutical preparations. They preferably bring about the quick introduction and development of diuresis, without the therapeutically risky potassium excretion known in the prior art, which has been considered a serious disadvantage. The same holds for magnesium.

The action of the compositions of the present invention is also superior to those of the individual active components.

The pharmaceutical preparations of the present invention comprise in a preferred embodiment, furosemide and the pteridine compounds of the general formula I in a weight ratio of 1:10 to 5:1 preferably 1:4 to 2:1. The dosages of the pharmaceutical preparations of the present invention are adjusted according to the nature and seriousness of the illness, the age and disposition of the patient, as well as relevant individual factors to be taken into consideration. The dosage is purposely measured so that after administration of the combined pharmacological compounds of the present invention per application unit (ampoule) the same sodium-uretic effect is brought about as during monotherapy with furosemide and at the same time a potassium neutral diuresis is achieved. Normal dosages which bring about this therapeutic effect, contain for example up to 20-, or preferably about 15 mg furosemide and 10 to 200 mg in particular 10 to 60 mg of the compounds of the general formula I, preferably the sulfate half ester of 2,4,7-triamino-6-p-hydroxyphenylpteridines (compounds of the formula I A) and the physiologically unobjectionable salts derived thereof.

The new pharmaceutical compositions may be prepared in a normal, well known manner and may contain the standard carriers and additives. The preferred administration form is parenteral, although oral administration is not excluded when it is necessary to do so.

The preparation of the compounds of the general formula I A, is well known or it is possible to carry it out using well known methods. The preparation of the compounds of the general formula I B, can be carried out by known methods, such as for example (a) through reaction of the compound 2,4,6-triamino-5-nitrosopyrimidine (hereinafter referred to as Compound of formula II) with a substituted phenylacetonitrile compound of the formula III

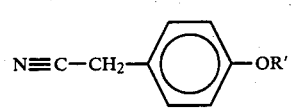 (III)

wherein R' has the meaning described above; or as a somewhat less general useful method, (b) through reaction of a compound of the general formula IV

 (IV)

wherein R' has the meaning mentioned above and wherein X stands for a leaving group useful for acylation-alkylation, preferably chlorine, or bromine; or XR' stands for the acid anhydride of the group R', with an appropriate salt of 2,4,7-triamino-6-(p-hydroxy-phenyl)-pteridine, such as for example the sodium, potassium or appropriate inert ammonium salts (hereinafter: compound of formula V), if necessary in combination with acid acceptors, or starting from 2,4,7-triamino-6-(p-hydroxyphenyl)-pteridine, through condensation with a compound of the formula IV which contains a COOH group, with help of a condensation agent such as for example dicyclohexylcarbodiimide (DCC) in a known manner.

The choice for the method of preparations as well as the reaction conditions for the compounds of the general formula I B will depend among other things on considerations respecting the relative availability of the starting products of the formulas II, III, IV, as well as the possibility of the formation of side products (such as for example the reaction of the amino functions) and easiness of the separation and purification processes. It will be taken into account for example that under the conditions of synthesis according to the variant of preparation (a) the substituents R' have to be generally stable.

The preparation of the compounds of the general formula I according to method (a) may be carried out as follows.

The compounds of formula II is reacted in an inert reaction medium, appropriate under the reaction condition, such as for example dimethylformamide or N,N-dimethyl-acetamide, preferably in the presence of an alkali metal hydroxide or -amide, or an alkali alcoholate of a lower alcohol such as for example in an alkoxy alkanol, such as 2-ethoxyethanol, or in methanol, and at elevated temperatures, if necessary in suspension with a compound of the general formula III.

The reaction times are as a rule usually as short as possible, for example when working at reflux temperatures. The work up can be carried out by standard methods.

The decomposition of the adduct and/or the end product can be prevented by for example working at the lower ranges of the reaction temperatures, and through use of alkali metal alcoholates with poor nucleophiles, such as for example potassium-tert-butoxide.

The preparation of the compounds of the general formula I B according to method (b) can be carried out as follows.

To a compound of the general formula V in an appropriate inert solvent, such as for example in a nitrile such as acetonitrile; or an amide such as N,N-dimethylformamide, hexamethylphosphoric acid triamide; in an alcohol such as tert-butanol; an amine, such as pyridine, N,N-dimethylaniline; or if necessary in a mixture of solvents or also in suspension, is added, preferably while stirring, between room temperature and 120° C. or at the boiling point of the solvent media, the compound of the general formula IV, if necessary in an appropriate solvent, such as those described above, with addition of an acid acceptor, such as for example a tertiary amine, such as triethylamine, N,N-dimethylaniline, or N-methylmorpholine.

The reaction is then stirred until completion for a given time such as for example between 2 and 24 hours, and thereafter the mixture is worked up in standard fashion.

The starting materials of the general formula (II), (III), (IV) and (V) are known, or they can be prepared according to known methodology or in analogy to known methodologies.

The compounds of general formula (I) are as a rule crystalline, relatively high melting compounds (partially with decomposition). They may be recrystallized for example from aqueous solution, if necessary with addition of formamide, acetonitrile, and also in the presence of acid, such as formic acid, acetic acid or phosphoric acid.

Having generally described this invention, a further understanding can be obtained by reference to certain specific examples which are provided herein for purposes of illustration only and are not intended to be limiting unless otherwise specified. These examples describe the preparation of compounds of the general formula (I). Temperatures are given in degrees centigrade and are uncorrected.

1. Preparation of 2,4,7-Triamino-6-(p-acetoxy-phenyl)-pteridine 410 mg metallic sodium were dissolved while stirring in 100 ml of 2-ethoxy ethanol. Thereafter, 1100 mg 2,4,6-Triaminonitrosopyrimidine are added while stirring together with 1140 mg p-acetoxybenzylcyanide and the mixture is heated while stirring up to the boiling point. The color of the mixture changed from violet to brown. After two hours boiling under reflux, the heat is turned off and the reaction mixture is allowed to cool. Thereafter, 70 to 80% of the 2-ethoxyethanol is distilled under the vacuum of the water system, and the residue is taken up in 500 mls of water. After four-fold extraction with ether the pH is adjusted to pH 5 with 2 N hydrochloric acid. The precipitate is filtered, it is washed with a small amount of ice-cold acetone and recrystallized from 10% acetic acid. Further purification can be carried out over a silica gel column. The title compound obtained melts at 319°–321° C. (carbonization).

The reaction can also be carried out with use of alkali alcoholate in methanol.

2. Preparation of 2,4,7-triamino-6-(p-2-hydroxyethoxyphenyl)-pteridine 460 mg metallic sodium were dissolved while stirring in 150 ml 2-ethoxyethanol. Thereafter to it was added while stirring 3.1 g (0.02 mole) of triaminonitrosopyrimidine and 2.5 g (0.02 mole) p-(2-hydroxyethoxy)-phenyl acetonitrile and the mixture was stirred and heated in the water bath at 60° C. The color of the mixture changed from violet to light brown. After 14 hours of stirring, the reaction was stopped. The mixture is then allowed to cool. Unreacted 2,4,6-triaminonitrosopyrimidine is filtered and the clear solution is evaporated and its volume reduced. The precipitate was taken up in hot acetone and by addition of petroleum ether, the raw product precipitated. The purification consisted of one recrystallization in butanol and also by passage through a silica gel column (Kieselgel 60, Merck). The title compound is obtained as yellowish-brown crystals.

Decomposition starts at 300° C.

$R_f$ values: 0.55 in elution medium chloroform/methanol (70:30) on silica gel-thin layer plates.

$C_{14}H_{15}N_7O_2$ (MW 313.3)

3. Preparation of 2,4,7-triamino-6-(p-2,3-dihydroxypropoxyphenyl)-pteridine

In an analogy to the compound in Example 2, it is also possible to prepare 2,4,7-triamino-6-(p-2,3-dihydroxy-propoxy-phenyl)-tperidine.

$R_f$ value: 0.5 in elution medium chloroform/methanol (70:30) in silica gel thin layer plates.
$C_{15}H_{17}N_7O_3$ (MW 341.3).

4. Preparation of 2,4,7-triamino-6-(p-succinoyl-phenyl)-pteridine

To dry acetone was added 0.63 g (0.0055 moles) of succinic acid, 1.35 g (0.005 Moles) of p-hydroxytriamterene as well as 1.12 g (0.05 moles) dicyclohexylcarbodiimide and it was heated for 14 days under water exclusion and boiling. The reaction was interrupted and the solvent was separated. The resulting precipitate was washed several times with ether. The remaining precipitate was taken up in a small amount of DMF (5–10 ml) and diluted with a 4-fold volume of acetone.

The solution is then added to a column of sephadex LH20 (Product of Pharmacia) suspended in acetone. The final product appears upon elution after a first fraction. It is obtained through evaporation of the acetonic solution.

$R_f$ value: 0.30 in an elution agent of chloroform/methanol (70:30) in silicagel thin layer plates.

5. Preparation of 2,4,7-triamino-6-(p-adipinoyl-phenyl)-pteridine

In analogy to the preparation in example 4 it is also possible to prepare 2,4,7-triamino-6-(p-adipinoyl-phenyl)-pteridine.

$R_f$ value=0.31 in an elution medium of chloroform/methanol (70:30) on a silica gel thin layer plate.

The preparation of the starting materials of the general formula (III) can be carried out for example as in the following examples:

Preparation of p-(2-Hydroxyethoxy)-phenylacetonitrile 5 g p-hydroxyphenylacetonitrile were dissolved in 250 ml methylethylketone. 7 g of 2-bromoethanol and 23 g potassium carbonate were added thereto. The mixture was stirred for 48 hours under reflux. At the end of the reaction the potassium carbonate and the produced potassium bromide were filtered. The precipitates were washed with acetone and the acetone wash was added to the reaction mixture. The clear solution was reduced to about 10–15 ml. It was then taken up in ether and shaken with 1/100 N sodium hydroxide.

The ether phase was dried over sodium carbonate and the ether was then distilled. The title compound is obtained as a slightly yellowish oil.

$R_f$ value: 0.70 in elution medium acetone/carbontetrachloride (1:1) on silica gel thin layer plates.

Preparation of p-(2,3-dihydroxypropoxy)-phenylacetonitrile:

In analogy to the p-(2-hydroxyethoxy)-phenylacetonitrile, it is also possible to prepare p-(2,3-dihydroxypropoxy)-phenylacetonitrile, wherein the shaking is carried out with water instead of sodium hydroxide. The product can then be found in the aqueous phase, which upon evaporation yields a colorless crystalline precipitate.

$R_f$ value: 0.60 in an elution medium of acetone/carbontetrachloride (1:1) on silica gel thin layer plates.

6. Preparation of 2,4,7-triamino-6-(4-β-dimethylamino-ethoxyphenyl)-pteridine 0.03 moles of metallic sodium were dissolved in 150 ml of 2-ethoxyethanol. Thereto was added 0.013 moles (3.1 g) of p-(β-dimethylaminoethoxy)-phenylacetonitrile as its hydrochloride and 0.01 moles (1.45 g) of 2,4,6-triamino-5-nitrosopyrimidine. The mixture was stirred for 48 hours at 60°–65° with exclusion of moisture. The reaction mixture was then centrifuged hot, the resulting solution was then mixed with petroleum ether until beginning of turbidity. Through standing in the refrigerator, the precipitation was completed. The precipitate is filtered and recrystallized from N-butanol. The title compound is obtained as yellow crystals.

Melting point 278°–281° C. (dec.)
$R_f$ value: 0.47 in an elution medium of methanol/chloroform/concentrated aqueous ammonia (4:4:1) on silica gel-thin layer plates.
MW 340.39 $C_{16}H_{20}N_8O$.

7. Preparation of 2,4,7-triamino-6-(4-β-N-piperidinylethoxyphenyl)-pteridine The title compound can prepared in analogy to example 6 but with utilization of p-(β-N-piperidinylethoxy)-phenylacetonitrile).

$R_f$ value: 0.64 in a elution agent of methanol/chloroform/concentrated aqueous ammonia (4:4:1) on silica gel-thin layer plates.
MW 380.45 $C_{19}H_{24}N_8O$.

Method for the preparation of a compound of general formula III (prepared for example in basic ether)

0.04 moles of p-hydroxyphenyl acetonitrile, 0.05 moles of the corresponding β-chloroethylamine as its hydrochloride, 0.1 moles potassium carbonate (dry) were mixed in 200 ml of dry acetone for 24 hours at 40°–45° and for further 24 hours in slightly boiling acetone.

The acetone was then removed in the rotary evaporator. The residue is taken up in 100 ml of water, acidified with concentrated hydrochloric acid up to a pH of 1–2, shaken twice with about 100 ml of ether. The ether contains the nonreacted phenol, which can be reutilized as mentioned above.

The aqueous solution was brought with about 8 N potassium hydroxide to a pH of about pH 12 and was shaken once with ether. The ether was dried over sodium carbonate and the basic ether was treated with dry HCl gas and the product precipitated at the hydrochloride.

The purification consisted of recrystallization from ethanol/ethylacetate.

Following the aforementioned descriptions the following examples were prepared.

8. p-(β-dimethylaminoethoxy)-phenylacetonitrile
MW 204.27, $C_{12}H_{16}N_2O$,
9. Hydrochloride
MW 240.735, $C_{12}H_{17}N_2OCl$,
10. p-(β-N-piperidinylethoxy)-phenylacetonitrile
MW 244.33, $C_{15}H_{20}N_2O$,
11. Hydrochloride
MW 280.8, $C_{15}H_{21}N_2OCl$.

Preparation of a combination according to the present invention, in an administration form useful for intravenous dispensation, of the sulfate half ester of 2,4,7-triamino-6-(p-hydroxyphenyl)-pteridine with furosemide 20 mg of 2,4,7-triamino-6-(p-hydroxyphenyl)-pteridine-sulfate half ester were mixed with 0.6 ml of a solution 0.1 molar of 2-methylaminoethanol (0.00006 moles) and filled with 50% aqueous polyethylene glycol 400 to a volume of 4 ml. To the resulting clear solution were added 15 mg of furosemide, which went fully into solution. So far as the used solutions were sterile and were treated in sterile fashion, the final solution is fully appropriate for the intravenous administration form.

Having now fully described this invention it will become readily apparent to one skilled in the art that many changes and modifications can be made thereto without departing from the spirit or scope of the invention set forth herein.

What is claimed as new and intended to be covered by Letters Patent is:

1. A diuretically active pharmacological composition, which is effective to produce a sodium uretic effect and at the same time a potassium neutral diuresis, which comprises 4-chloro-N-furfuryl-5-sulfamoyl anthranilic acid (furosemide) together with at least one compound of formula I:

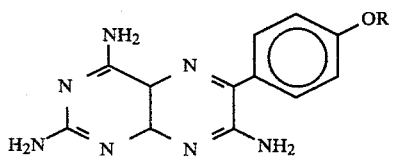

wherein
R is a radical R', wherein:
R' is selected from the group consisting of a radical of the formula:

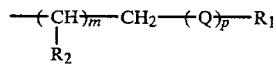

wherein
$R_1$ is hydrogen, methyl or ethyl, $R_2$ is a OH group, hydrogen or an alkyl group with 1 to 4 carbon atoms, Q is oxygen, sulfur or a radical of the formula —$NR_3$, wherein $R_3$ has the same meaning as $R_1$, or Q together with the radical $R_1$ forms an ammonium ion of the formula

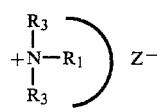

or
Q together with the radical $R_1$ forms a heterocyclic ring selected from the group consisting of pyrrolidinyl, piperidinyl, morpholinyl and piperazinyl, wherein $Z^-$ is a pharmacologically unobjectionable anion and m is 0, 1, 2 or 3; p is 0 or 1;
or
R' is a radical of the formula —$(CH_2)_nC(O)Y$, wherein n=0, 1, 2, 3 or 4; and Y is a —OH-group or a pharmacologically unobjectionable salt thereof, or Y stands for a group of the formula —$NR_4R_5$, wherein $R_4$ and $R_5$ independently of each other stand for hydrogen or a branched or unbranched alkyl radical of 1 to 4 carbon atoms, or they are a radical of the formula —$(O)_r$—$R_6$, wherein $R_6$ stands for an alkyl radical with 1 to 6 carbon atoms; or they are a radical of the formula —$(CH_2)_q$—$R_7$, wherein q is 0, 1 or 2, and $R_7$ is a heterocyclic ring selected from the group of morpholinyl-, pyrrolidinyl-, piperidinyl-, or piperazinyl-, which may be bound through a carbon atom or through a nitrogen atom, wherein in the latter case q is not equal to 0, and which formally form an ammonium compound through juxtaposition of a compound of the formula $R_1'Z'$, wherein $R_1'$ and $Z'$ have the same meanings as $R_1$ and Z, and r equals 0 or 1, or
R' stands for a radical of the formula

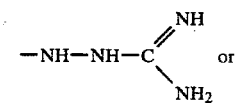

or it stands for a radical of the formula

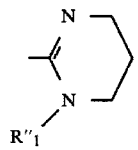

wherein
$R_1''$ has the same meaning as $R_1$ or R' stands for a radical of the formula

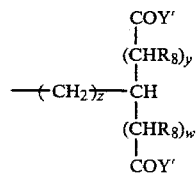

wherein
Y' has the same meaning as Y, $R_8$ stands for hydrogen or an OH-group; v, w and z are 0, 1 or 2, or
R' stands for a radical of the formula —C(O)—$(CHR'_8)_s$—C(O)—Y''', wherein s=1, 2 or 3, and $R_8'$ and Y''' have the same meaning as $R_8$ and Y respectively, or R' stands for a radical of the formula

wherein M is hydrogen or a physiologically unobjectionable cation.

2. The composition of claim 1 wherein said pharmaceutical carrier is appropriate for intravenous dispensation.

3. The compositions of claim 1 wherein the weight ratio of furosemide to the compounds of formula (I) is 1:10 to 5:1.

* * * * *